US008625867B2

(12) United States Patent
Moriya

(10) Patent No.: US 8,625,867 B2
(45) Date of Patent: Jan. 7, 2014

(54) MEDICAL IMAGE DISPLAY APPARATUS, METHOD, AND PROGRAM

(75) Inventor: Yoshiyuki Moriya, Minato-ku (JP)

(73) Assignee: FUJIFILM Corporation, Tokyo (JP)

(*) Notice: Subject to any disclaimer, the term of this patent is extended or adjusted under 35 U.S.C. 154(b) by 106 days.

(21) Appl. No.: 13/496,752

(22) PCT Filed: Sep. 15, 2010

(86) PCT No.: PCT/JP2010/005639
§ 371 (c)(1),
(2), (4) Date: Mar. 16, 2012

(87) PCT Pub. No.: WO2011/033769
PCT Pub. Date: Mar. 24, 2011

(65) Prior Publication Data
US 2012/0183188 A1 Jul. 19, 2012

(30) Foreign Application Priority Data

Sep. 17, 2009 (JP) ................................. 2009-215100
Mar. 24, 2010 (JP) ................................. 2010-067799

(51) Int. Cl.
G06K 9/00 (2006.01)

(52) U.S. Cl.
USPC ............................ 382/128; 128/922; 707/609

(58) Field of Classification Search
USPC ......... 382/100, 128, 129, 130, 131, 132, 133; 128/922; 707/609, 705, 713, 715
See application file for complete search history.

(56) References Cited

U.S. PATENT DOCUMENTS

| 5,499,323 | A | 3/1996 | Doi et al. |
| 5,644,689 | A | 7/1997 | Ban et al. |
| 6,747,561 | B1* | 6/2004 | Reeves ....................... 340/573.1 |
| 7,187,790 | B2* | 3/2007 | Sabol et al. ................... 382/128 |
| 7,301,535 | B2* | 11/2007 | Shen ............................. 345/424 |
| 7,319,781 | B2* | 1/2008 | Chen et al. .................... 382/128 |
| 7,607,079 | B2* | 10/2009 | Reiner .......................... 715/233 |
| 8,064,663 | B2* | 11/2011 | Van Hoe et al. .............. 382/128 |
| 2002/0181754 | A1 | 12/2002 | Masumoto et al. |
| 2005/0065424 | A1* | 3/2005 | Shah et al. .................... 600/407 |
| 2005/0226405 | A1 | 10/2005 | Fukatsu et al. |

(Continued)

FOREIGN PATENT DOCUMENTS

| JP | 05-189541 A | 7/1993 |
| JP | 07-021405 A | 1/1995 |

(Continued)

OTHER PUBLICATIONS

International Search Report of PCT/JP2010/005639 dated Nov. 9, 2010.

Primary Examiner — Anand Bhatnagar
(74) Attorney, Agent, or Firm — Sughrue Mion, PLLC

(57) ABSTRACT

Storing a second image reconstructed from a plurality of images, including a first image, and an image reading report that includes a lesion character representing a lesion area in the first image. Associating the lesion character with a position of the lesion area and storing the position in the second image corresponding to the position of the lesion area as a link position. Displaying a link character constituted by the lesion character, a position indicator indicating the link position corresponding to the position of the lesion area represented by the link character, and an association indicator indicating the link character and position indicator in association with each other in the second medical image.

9 Claims, 15 Drawing Sheets

(56) References Cited

U.S. PATENT DOCUMENTS

| | | |
|---|---|---|
| 2006/0271403 A1 | 11/2006 | Iwasa et al. |
| 2007/0219651 A1 | 9/2007 | Kawakami et al. |
| 2007/0237376 A1 | 10/2007 | Yoshida |
| 2007/0237978 A1* | 10/2007 | Schubert ................ 428/607 |

FOREIGN PATENT DOCUMENTS

| | | |
|---|---|---|
| JP | 2001-137230 A | 5/2001 |
| JP | 2001-283191 A | 10/2001 |
| JP | 2002-345807 A | 12/2002 |
| JP | 2004-141612 A | 5/2004 |
| JP | 2005-301453 A | 10/2005 |
| JP | 2007-012044 A | 1/2007 |
| JP | 2007-264773 A | 10/2007 |
| JP | 2007-275558 A | 10/2007 |
| JP | 2008-043564 A | 2/2008 |
| JP | 2008-253293 A | 10/2008 |

* cited by examiner

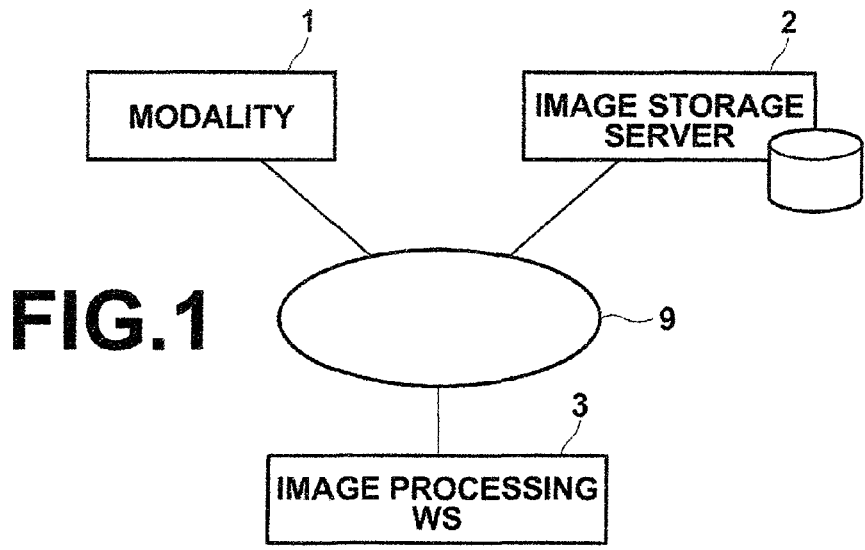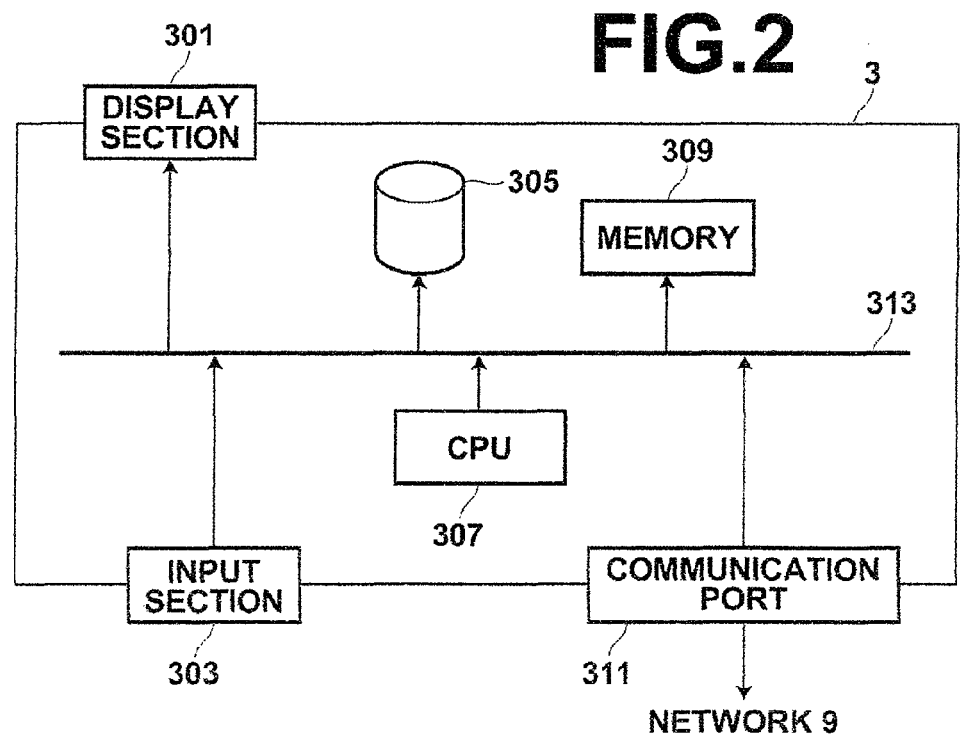

FIG.13

| ORGAN | LUMINANCE VALUE (LOW) | LUMINANCE VALUE (HIGH) | LESION NAME | | | |
|---|---|---|---|---|---|---|
| | | | BRACKET | PNEUMOTHORAX | LUNG EMPHYSEMA | BRONCHODILATION |
| LUNG | -2000 | 0 | PLEURAL EFFUSION | TUMOR | | |
| | -20 | 70 | NODULE | GGO | INFILTRATIVE SHADOW | |
| | 50 | 150 | CALCIFICATION | | | |
| | 100 | 1000 | | | | |
| LIVER | | | | | | |
| BONE | | | | | | |
| HEART | | | | | | |

FIG.17

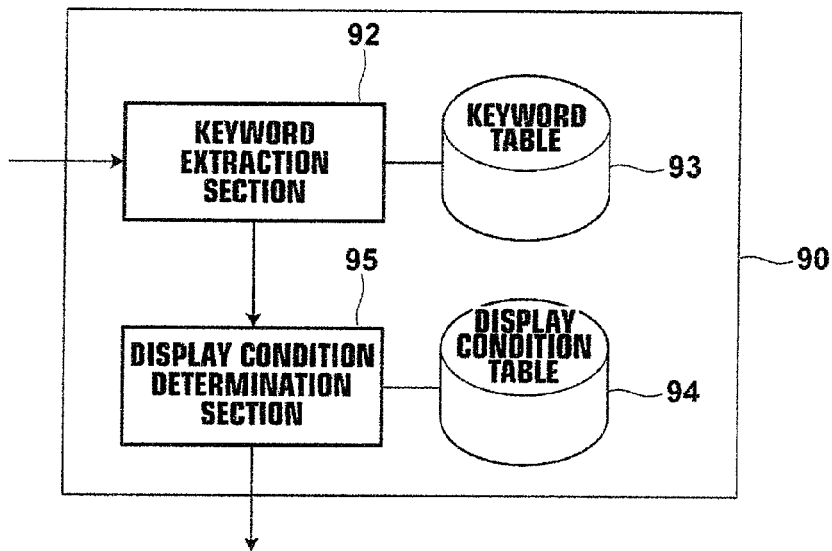

FIG.18

| KEYWORD | LESION CHARACTER |
|---|---|
| LUNG | LUNG/LUNG FIELD/RIGHT LUNG/LEFT LUNG/UPPER LOBE/MIDDLE LOBE/LOWER LOBE - - - - - |
| LIVER | LIVER/RIGHT HEPATIC LOBE/LEFT HEPATIC LOBE/CAUDATE HEPATIC LOBE/DORSOLATERAL SEGMENT OF LEFT HEPATIC LOBE |
| BRAIN | HEAD REGION/BRAIN/CEREBRUM/FRONTAL LOBE |
| VERTEBRAL DISK | VERTEBRAL DISK |
| NODULE | NODULE - - - - - |
| TUMOR | TUMOR - - - - - |
| GROUND GLASS OPACITY | GROUND GLASS OPACITY |
| STENOSIS | STENOSIS |
| INFARCTION | INFARCTION |
| HERNIA | HERNIA |
| - - - - - | |

FIG.19

| DISPLAY CONDITION ID | KEYWORD | TYPE OF IMAGE | COLOR TEMPLATE | DISPLAY POSITION INFORMATION |
|---|---|---|---|---|
| 101 | BLOOD VESSEL | VR | Cr1 | (0,0), W=512 H=512 |
| 102 | LIVER | VR | Cr2 | (0,0), W=512 H=512 |
| 103 | ... | ... | ... | ... |

| DISPLAY CONDITION ID | KEYWORD | IMAGE PROCESSING 1 | IMAGE PROCESSING 2 |
|---|---|---|---|
| 201 | HEART | EXTRACT HEART / EXTRACT CORONARY ARTERY | DISTINGUISHABLY DISPLAY EXTRACTED ANATOMICAL STRUCTURE |
| 202 | LIVER | EXTRACT LIVER | HIDE OTHER THAN EXTRACTED ANATOMICAL STRUCTURE |
| 203 | SPLEEN | EXTRACT SPLEEN | HIDE OTHER THAN EXTRACTED ANATOMICAL STRUCTURE |
| 204 | BLOOD VESSEL | EXTRACT BONE | HIDE EXTRACTED ANATOMICA |

~94b

MEDICAL IMAGE DISPLAY APPARATUS, METHOD, AND PROGRAM

CROSS REFERENCE TO RELATED APPLICATIONS

This application is a National Stage of International Application No. PCT/JP2010/005639 filed Sep. 15, 2010, claiming priority based on Japanese Patent Application Nos. 2009-215100 filed Sep. 17, 2009 and 2010-067799 filed Mar. 24, 2010, the contents of all of which are incorporated herein by reference in their entirety.

BACKGROUND OF THE INVENTION

1. Field of the Invention

The present invention relates to a medical image display apparatus, method, and program, and more particularly to a medical image display apparatus, method, and program for displaying, when a lesion character in an image reading report is specified, an image of the lesion area.

2. Description of the Related Art

Recently, medical image display technologies for reconstructing and displaying medical images have been evolving and serving as assistance in image diagnosis performed in the medical field as described, for example, in Japanese Unexamined Patent Publication Nos. 5 (1993)-189541 and 7 (1995)-021405.

In image diagnoses using medical images, in general, diagnosticians make diagnoses with reference to image reading reports generated by radiologists. Some image reading reports allow a reference image to be linked to a character string in the reports as described, for example, in Japanese Unexamined Patent Publication No. 2005-301453. Use of such image reading reports allows the radiological image reader to display a corresponding image by simply specifying a character described in the report.

Although, Japanese Unexamined Patent Publication No. 2005-301453 allows reference to the medical image corresponding to the character string in the image reading report, the position where the lesion area described in the image reading report is present or the character string representing the corresponding lesion cannot be known from the medical image itself.

Further, it has been difficult to accurately recognized as to which position in the medical image the lesion described in the image reading report corresponds to, as one medical image is linked to one character string in the image reading report.

In view of the circumstances described above, it is an object of the present invention to provide a medical image display apparatus, method, and program that allows more accurate image interpretation by displaying lesion information described in an image reading report in a medical image.

SUMMARY OF THE INVENTION

A medical image display apparatus of the present invention is an apparatus, including a medical image storage unit for storing a first medical image and a second medical image reconstructed from a plurality of medical images, including the first medical image;

an image reading report storage unit for storing an image reading report that includes a lesion character representing lesion contents of a lesion area in the first medical image;

a lesion storage unit for storing the lesion character and a position of the lesion area in association with each other;

a link position storage unit for calculating a position in the second medical image corresponding to the position of the lesion area and storing the calculated position as a link position;

a medical image display unit for obtaining the second medical image from the medical image storage unit and displaying the obtained image; and a link information display unit for displaying a link character constituted by the lesion character and a position indicator indicating the link position corresponding to the position of the lesion area represented by the link character in the second medical image in association with each other.

A medical image display method of the present invention is a method, including the steps of:

storing a first medical image and a second medical image reconstructed from a plurality of medical images, including the first medical image;

storing an image reading report that includes a lesion character representing lesion contents of a lesion area in the first medical image;

storing the lesion character and a position of the lesion area in association with each other;

calculating a position in the second medical image corresponding to the position of the lesion area and storing the calculated position as a link position;

obtaining the second medical image from the medical image storage unit and displaying the obtained image; and displaying a link character constituted by the lesion character and a position indicator indicating the link position corresponding to the position of the lesion area represented by the link character in the second medical image in association with each other.

A medical image display program of the present invention is a program for causing a computer to function as:

a medical image storage unit for storing a first medical image and a second medical image reconstructed from a plurality of medical images, including the first medical image;

an image reading report storage unit for storing an image reading report that includes a lesion character representing lesion contents of a lesion area in the first medical image;

a lesion storage unit for storing the lesion character and a position of the lesion area in association with each other;

a link position storage unit for calculating a position in the second medical image corresponding to the position of the lesion area and storing the calculated position as a link position;

a medical image display unit for obtaining the second medical image from the medical image storage unit and displaying the obtained image; and a link information display unit for displaying a link character constituted by the lesion character and a position indicator indicating the link position corresponding to the position of the lesion area represented by the link character in the second medical image in association with each other.

The "first medical image" as used herein may be any medical image as long as it includes a lesion area, and various types of medical images may be used. For example, typical medical images that may be used as the first medical image may include but not limited to two-dimensional medical images obtained by CT, MRI, PET, ultrasonic diagnostic equipment, and the like. The term "reconstructed second medical image" as used herein refers to three-dimensional medical images reconstructed from multiple slice images obtained by CT, MRI, PET, ultrasonic diagnostic equipment, or the like, or two-dimensional medical images. Typical reconstructed images include those represented by volume rendering, ray summation, maximum intensity projection (MIP), and multi planar reformat (MPR).

The term "lesion character" as used herein refers to a character that includes a disease name, keyword or symbol representing a disease name, or abbreviation thereof. Further, the lesion name may include an organ name.

The "position of the lesion area" as used herein may be a point indicating an arbitrary position in the lesion area or the position indicating the lesion area itself. The area may be indicated by various methods, including a circle, rectangle, arrow, closed surface, and the like. As for the arbitrary point, the gravity center of the area, center of the area, or the like may be selected as appropriate.

The term "displaying a link character constituted by the lesion character and a position indicator indicating the link position corresponding to the position of the lesion area represented by the link character in the second medical image in association with each other" as used herein may be achieved by any method as long as it may display the link character and corresponding position indicator in a distinguishable manner. For example, an association index such as a leading line that associates the link character with the corresponding position indicator may be used, or the link character may be displayed adjacent to the corresponding position indicator. Further, the term "displaying in association with each other" may include the case in which the link character and the corresponding position indicator can be identified, such as the case in which only one link character and only one position indicator are displayed, even if the association indicator is not used or the link character is not displayed adjacent to the position indicator.

The second medical image may be a three-dimensional image.

Further, the link position storage unit may be a unit that stores the lesion character and a word or phrase before and after the lesion character from the image reading report stored in the image reading report storage unit, and the link information display unit may be a unit that displays the word or phrase before and after the lesion character in addition to the link character.

The apparatus may further include a link character specifying unit for specifying the link character in the second medical image and an image reading report display unit for displaying the image reading report, the link character may be a character linked to the lesion character in the image reading report by a hyperlink, and the image reading report display unit is preferable to be a unit that, in response to the specification of the link character in the second medical image, additionally displays the entirety of the image reading report that includes the lesion character corresponding to the specified link character with the lesion character corresponding to the specified link character in the additionally displayed image reading report being highlighted.

Here, the "link character" linked by a hyperlink is displayed in a manner distinguishable from a non-linked character using any known method, such as coloring of the lesion character, coloring of the background, or use of an underline, blinking, boldface, different font type or size, or frame for the lesion character.

The character of the "link character" may include a character string, symbol, or numerical character.

The term "with the lesion character being highlighted" as used herein refers to that the lesion character is displayed in an emphasized manner so as to be distinguishable from the other lesion characters using any known method such as coloring of the lesion character, coloring of the background, or use of an underline, blinking, boldface, different font type or size, or frame for the lesion character.

The term "specification of the link character" as used herein refers to that the link character is specified by a mouse, keyboard, or other input devices.

The lesion character may be a character linked to the first medical image by a hyperlink, the medical image display unit may be a unit that displays the first medical image, other than the second medical image, in response to the specification of the lesion character in the additionally displayed image reading report, and the link information display unit may be a unit that further displays an indicator indicating the position of the lesion area in the first medical image.

The image reading report display unit may be a unit that displays, in conjunction with the image reading report, an attached image which is a reduced image of the medical image that includes the lesion area corresponding to the specified link character.

The image reading report may include a plurality of image reading reports with respect to past medical images or with respect to a plurality of different lesion positions.

According to the image reading report display apparatus, method, and program of the present invention, an image reading report in which a position of a lesion area in a first medical image and a lesion character representing the lesion are associated is stored, the lesion character and the position of the lesion area are stored in association with each other, and a link character constituted by the lesion character and a position indicator indicating the link position corresponding to the position of the lesion area represented by the link character are displayed in a second medical image reconstructed from a plurality of medical images, including the first medical image, in association with each other. This allows the position of the lesion area and a character string representing the lesion to be referenced in the second medical image, whereby the position of the lesion area may be accurately recognized.

In the case where the second medical image is a three-dimensional medical image, the position of the lesion area may be associated with the three-dimensional image and observed, so that the position of the lesion area may be recognized more accurately.

In the case where the link position storage unit is a unit that stores the lesion character and a word or phrase before and after the lesion character from the image reading report stored in the image reading report storage unit, and the link information display unit is a unit that displays the word or phrase before and after the lesion character in addition to the link character, not only the lesion character representing a lesion but also a word or phrase before and after the lesion character are displayed. This allows more information described in the image reading report to be obtained from the medical image, resulting in accurate image reading.

In the case where the apparatus further includes a link character specifying unit for specifying the link character in the second medical image and an image reading report display unit for displaying the image reading report, the link character is a character linked to the lesion character in the image reading report by a hyperlink, and the image reading report display unit is a unit that, in response to the specification of the link character in the second medical image, additionally displays the entirety of the image reading report that includes the lesion character corresponding to the specified link character with the lesion character corresponding to the specified link character in the additionally displayed image reading report being highlighted, the entirety of the image reading report may be displayed in response to the specification of the link character in the medical image, so that the entire image reading report may be referenced as required, whereby image reading may be performed easily.

In the case where the lesion character is a character linked to the first medical image by a hyperlink, the medical image display unit is a unit that displays the first medical image, other than the second medical image, in response to the specification of the lesion character in the additionally displayed image reading report, and the link information display unit is a unit that further displays an indicator indicating the position of the lesion area in the first medical image, in addition to the position of the lesion area in the second medical image, the corresponding position of the lesion area in the medical image may be recognized accurately, resulting in accurate medical image reading.

In the case where the image reading report display unit is a unit that displays, in conjunction with the image reading report, an attached image which is a reduced image of the medical image that includes the lesion area corresponding to the specified link character, the attached image that includes the position of the lesion area may be referenced easily, whereby image reading may be performed easily.

In the case where the image reading report includes a plurality of image reading reports with respect to past medical images or with respect to a plurality of different lesion positions, information of a plurality of image reading reports may be referenced and image reading may be performed accurately.

BRIEF DESCRIPTION OF THE DRAWINGS

FIG. 1 is a schematic configuration diagram of a medical image display apparatus according to an embodiment of the present invention.

FIG. 2 is a block diagram, illustrating a configuration of a first embodiment.

FIG. 13 shows, by way of example, an association table associating lesion areas with lesion character candidates.

FIG. 17 is a functional block diagram of a display condition determination unit of the fifth embodiment.

FIG. 18 shows, by way of example, a keyword table.

FIG. 19 shows, by way of example, a display condition table of the fifth embodiment.

FIG. 20 shows, by way of example, a display condition table of a modification of the fifth embodiment.

DESCRIPTION OF THE PREFERRED EMBODIMENTS

Figure 3:
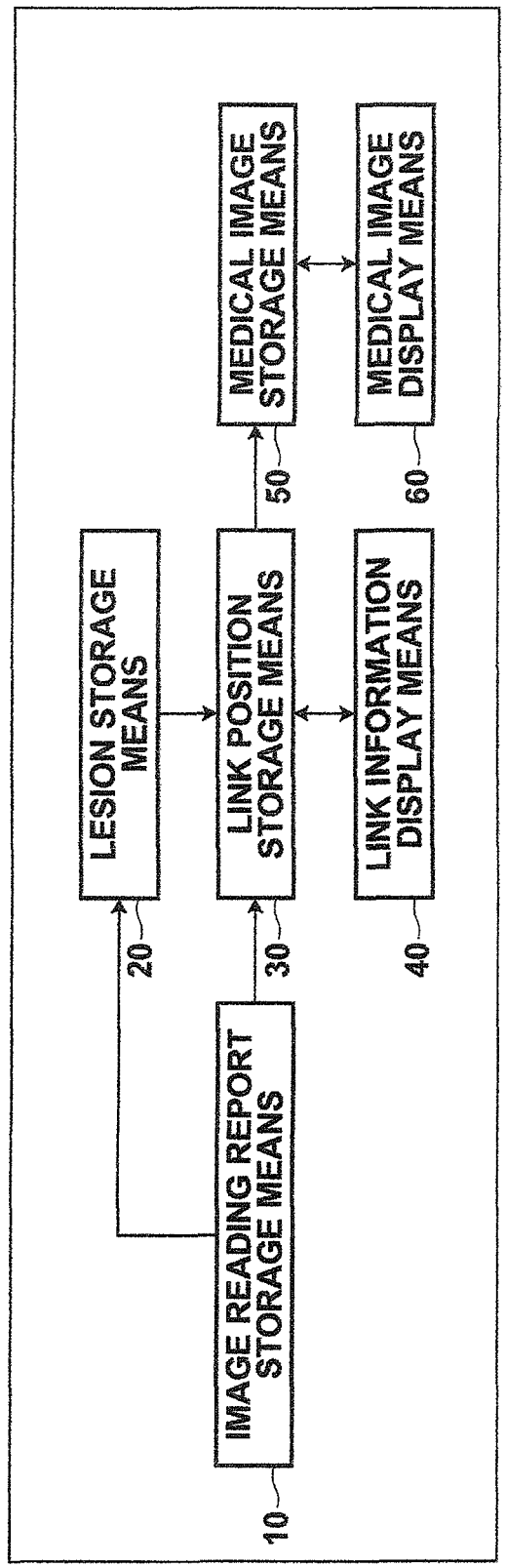
FIG. 3 is a functional block diagram of a medical image display function of the first embodiment.

FIG. 1 is a hardware configuration diagram of a medical image processing system, illustrating an overview thereof. As shown in FIG. 1, the system includes modality 1, image storage server 2, and image processing workstation 3 communicatively linked via network 9.

Modality 1 is equipment for obtaining a medical image V representing a subject, and more specifically it is CT, MRI, PET, ultrasonic diagnostic equipment, or the like.

Image storage server 2 is a computer for storing/managing a medical image V obtained by modality 1 and a medical image V generated in workstation 3 by image processing, and includes an external large capacity recording medium and database management software (for example, ORDB (object relational database) management software).

Image processing workstation 3 is a computer for performing image processing on a medical image V obtained from modality 1 or image storage server 2 in response to a request from a radiological image reader and displaying an image generated by the image processing.

The image data storage format and communication between each component of the system via network 9 is based on a protocol, such as DICOM (digital imaging and communications in medicine) or the like.

A portion of the system relevant to the medical image processing function according to a first embodiment of the present invention will now be described.

FIG. 2 is a schematic block diagram of workstation 3, illustrating the configuration thereof. As illustrated in FIG. 2, the medical image display apparatus according to an embodiment of the present embodiment is made up of image processing workstation 3 that includes display section 301, such as a liquid crystal monitor, for performing various types of display operations, input section 303 that includes a keyboard and mouse for performing various types of input operations, hard disk 305 for storing various types of programs for controlling the medical image display apparatus according to the present embodiment, including the medical image processing program of the present invention, and various types of data such as image data and the like, CPU 307 for controlling the medical image display apparatus according to the present embodiment through execution of the various types of programs, memory 309 serving as a work area during execution of a program, and communication interface 311 for connection to a network via bus 313.

In each embodiment, the function of the present invention is implemented by a computer with a program installed thereon from outside. Here, the program, including a group of other information, may be those provided by a recording medium, such as a CD-ROM, a flash memory, a FD, or the like, or supplied from an external recording medium through a network, and installed on the computer.

FIG. 3 is a functional block diagram illustrating a portion relevant to the medical image display function of the first embodiment of the present invention. As illustrated in FIG. 3, the medical image display apparatus of the present invention includes medical image storage means 50 for obtaining, via network 9, a first medical image and a second medical image reconstructed from a plurality of medical images, including the first medical image, in response to a request from modality 1 or image storage server 2, image reading report storage means 10 for storing an image reading report that includes a lesion character representing contents of a lesion area in the first medical image, lesion storage means 20 for storing a position of the lesion area and a lesion character in association with each other, link position storage means 30 for calculating a position in the second medical image corresponding to the position of the lesion area and storing the calculated position as a link position, medical image display means 60 for obtaining the second medical image from medical image storage means 50 and displaying the obtained image, and link information display means 40 for displaying a link character constituted by the lesion character and a position indicator indicating the link position corresponding to the position of the lesion area represented by the link character in the second medical image in association with each other.

Image reading report storage means 10 is mainly constituted by hard disk 305 and stores an image reading report that includes a lesion character representing lesion contents of a lesion area in a medical image V.

Lesion storage means 20 mainly constituted by hard disk 305 and stores the lesion character of the image reading report stored in image reading report storage means 10 and the position of the lesion area corresponding to the lesion character in association with each other.

Link position storage means 30 is mainly constituted by hard disk 305 and CPU 307, and calculates a lesion position in reconstructed second medical image 133 corresponding to the lesion position in the first medical image stored in lesion storage means 20.

Link information display means 40 is mainly constituted by display section 301, and displays a link character and a position indicator indicating the position of the associated lesion area in reconstructed medical image 133 in association with each other. The position indicator may be a circular mark like indicator 135C shown in FIG. 8, or any other known indicator capable of indicating a position, such as a point, crisscross, arrow, or the like. Further, in the case where a lesion area is indicated by various methods, including a circle, rectangle, arrow, closed surface, and the like, the position indicator may be used to indicate a particular point in the lesion area. The particular point may be selected from the gravity center, center, and point representing the characteristic of the lesion area as appropriate. The "displaying in association with each other" may be achieved by any method as long as it may display the link character and corresponding position indicator in association with each other in distinguishable manner. For example, the link character and the corresponding position indicator may be displayed by connecting them with a line, arrow, or association indicator of graphic, such as a speech balloon extending from the position indicator. Further, the link character may be displayed adjacent to the corresponding position indicator. Further, the term "displaying in association with each other" may include the case in which the link character and the corresponding position indicator can be identified, such as the case in which only one link character and only one position indicator are displayed, even if the association indicator is not used or the link character is not displayed adjacent to the position indicator.

Medical image storage means 50 is mainly constituted by hard disk and stores slice images from CT, MRI, PET, ultrasonic diagnostic equipment, or the like and three-dimensional medical images reconstructed from the slice images, or two-dimensional medical images. Typical reconstructed images include those represented by volume rendering, ray summation, maximum intensity projection (MIP), and multi planar reformat (MPR).

Medical image display means 60 is mainly constituted by communication interface 311 for obtaining a medical image V from network 9 and display section 301 for displaying the obtained medical image V, and display a medical image obtained from medical image storage means 50 on display section 301.

A method of generating an image reading report, a method of generating link information, and a method of displaying a medical image with the generated link information according to a first embodiment will be described briefly.

An example method for generating an image reading report of the first embodiment will be described with reference to FIG. 5.

Figure 5:
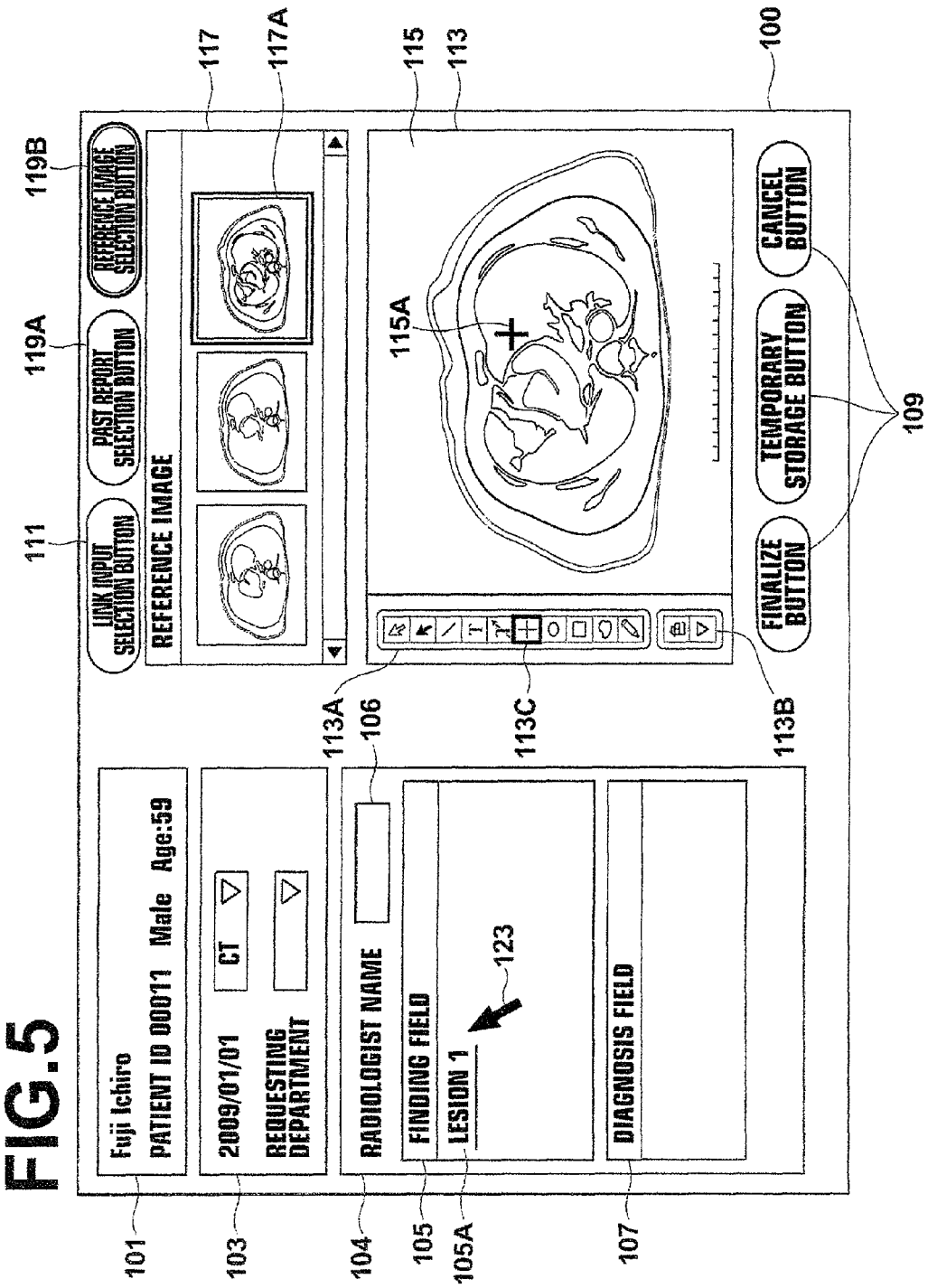
FIG. 5 is a conceptual diagram of a lesion character insertion screen of the first embodiment.

FIG. 5 is a conceptual diagram of an image reading report generation screen of the first embodiment. FIG. 5 shows image reading report generation screen 100 by way of example.

First, the layout of image reading report generation screen 100 shown in FIG. 5 will be described. Image reading report generation screen 100 shown in FIG. 5 includes patient information area 101 for entering patient information. For example, a patient name, patient ID, gender, age, and the like, which can be obtained from header information of DICOM, are displayed in the patient information area. In medical image information area 103 for indicating information of a medical image V, the date of the image, modality used, requesting department, and the like are entered from input section 303, such as the mouse or keyboard, or from header information of DICOM and displayed. Image reading report area 104 includes radiologist name field 106, finding field 105 which is an image reading report, and diagnosis field 107. A doctor or the like, as the operator, may enter or edit information in radiologist name field 106, finding field 105, and diagnosis field 107, using the mouse or keyboard.

Further, image reading report generation screen 100 may include image reading report editing buttons 109 for storing or cancelling an edited image reading report and various other function buttons as appropriate. In FIG. 5, a temporary storage button, finalize button, cancel button are shown, by way of example.

Image reading report generation screen 100 may include necessary buttons for referencing information, such as past report selection button 119A, reference image selection button 119B, and the like, as appropriate, and includes link input selection button 111 for enabling link input of an embodiment of the present invention. Such link input selection button 111 may by provided in various known forms within a range in which the purpose thereof is achieved.

When past report selection button 119A is selected, past reports are selectably displayed in reference image area 117. If reference image selection button 119B is selected, thumbnails of medical images V are selectably displayed in reference image area 117, as shown in FIG. 5.

Image reading report generation screen 100 further includes detailed image display area 113 and reference information such as thumbnails of medical images V, past reports, or the like, are displayed in reference image area 117 as appropriate. In the example shown in FIG. 5, thumbnail 121A is selected from a plurality of thumbnails representing medical images V in reference image area 117 and medical image 115 corresponding to thumbnail 121A is displayed in detailed image display area 113. Note that the plurality of thumbnails displayed in reference image area 117 may be those of medical images representing lesions included in one series of medical images V or those of medical images representing lesions included in a plurality of series of medical images V.

Detailed image display area 113 include, as appropriate, editing buttons 113A, 113B for processing and editing the medical image displayed therein.

Figure 4:
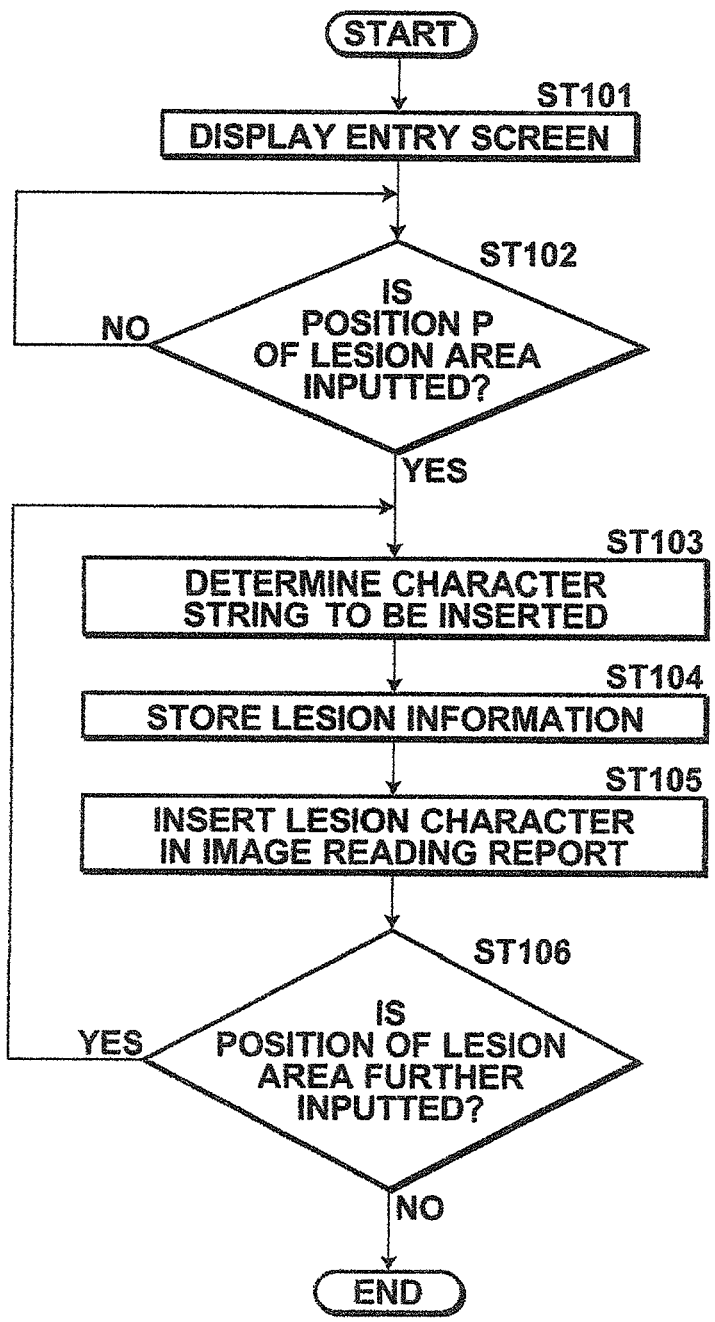
FIG. 4 is a flow diagram illustrating a process flow for inserting a lesion character in an image reading report of the first embodiment.

Next, a method of generating an image reading report having lesion character 105A will be described with reference to FIG. 4. FIG. 4 is a flowchart representing a method of generating an image reading report of the present embodiment. First, link input button 111 is selected by input section 303 to set the link input mode to ON (ST101). In order to input the position of a link input lesion, crosshair pointer 113C is selected from editing buttons 113A using input section 303. Then, a crosshair pointer is displayed and when the crosshair pointer is placed on the position of a lesion and clicked with the mouse, lesion position 115A is inputted (ST102 is YES).

When lesion position 115A is inputted, information including information indicating the storage location of medical image 115 that includes lesion position 115A and position information indicating the position of the lesion area in medical image 115, such as coordinates of the lesion area, is obtained. The position information may further include information obtained, for example, from header information of DICOM, such as image ID or the like. For example, in the case where the position of the lesion area is a point, the position information may be obtained as coordinate values in medical image 115, while if it is a circle, the position information may be obtained as coordinate values of the center of the circle and a length of the radius in medical image 115. If the position of the lesion is a diagram encircled by a straight line or curved line, information representing the diagram, such as an end point of the straight line in medical image 115 or a function representing the curved line, may be obtained, as appropriate, as the position information.

Then, a character string not yet used in finding field 105 is selected from predetermined character strings, and a character string to be inserted as lesion character 105A is determined (ST103).

The predetermined character string may be a character string, symbol, or numeric character, and (1) a fixed character string (2) if medical image 115 is a medical image constituting one series formed of a series of tomographic images, a combination of the medical image series number with a slice number or the like as information to identify a medical image that includes a lesion position (3) a pixel value of a lesion position (4) an anatomical region name of a lesion position such as left upper lung lobe, left lingular segment, or the like (5) coordinate values of a lesion position and (6) a combination thereof may be used.

In the case where a region name representing an anatomical region as shown in (4) above is to be inserted in finding field 105, as the character string, the character string may be extracted and inserted in the following manner. First, the organ to which the inputted lesion position belongs is extracted by computer aided diagnosis (CAD). The following specific techniques may be used for extracting the following: the techniques described in Japanese Unexamined Patent Publication Nos. 2001-137230 and 2008-253293 for lung fields; the techniques described in Japanese Unexamined Patent Publication Nos. 2001-283191 and 2002-345807 for livers; the technique described in Japanese Unexamined Patent Publication No. 2008-43564 for bones; and the technique described in Japanese Unexamined Patent Publication No. 2004-141612 for hearts. In addition, any other organ recognition technique may be used as long as it is capable of automatically extracting the organ to which the specified lesion position belongs. For example, the organ extraction described may be performed on a medical image that includes a lesion position and if the extracted organ includes the lesion position, the organ may be determined as the organ to which the lesion position belongs. The anatomical region name representing the organ may be inserted as the lesion character. In this case, the symptom or position of the lesion area may be assumed from the lesion character, as well as a linking operation may be implemented without inputting a lesion character from input section 303, so that the image reading report may be generated efficiently. Further, each organ or a region name representing a region of each organ may be used as the region name. For example, in the case of lungs, left lung or right lung may be used as the region name or otherwise further classified names of right upper lung lobe, right middle lung lobe, right lower lung lobe, left upper lung lobe, or left lower lung lobe may be used as the region name. Further, a region name classified by the lung segment, such as the superior lingular segment (S4) of left upper lung lobe or abbreviated names thereof may be used.

In the case where information, such as luminance value 203 of the image at the position of the lesion area, is further obtained, as the position information, the character string to be inserted may be determined in the following manner. As shown in FIG. 13, an association table of position of lesion area and lesion character candidate associating organ names, characteristic information 203 of positions of lesion areas, and lesion character candidates with each other is provided. In the table shown in FIG. 13, luminance values 203 of CT images are associated as the characteristic information 203 of the positions of lesion areas.

Figure 14:
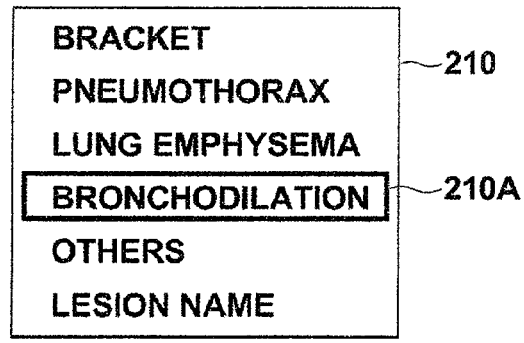
FIG. 14 shows, by way of example, a display of a list of lesion character candidates.

When a position of lesion area is inputted, the organ to which the inputted position of lesion area belongs is extracted using the specific extraction method described above, such as the computer aided diagnosis or the like. Then, the luminance value of the image at the inputted position of lesion area is obtained as the position information. As shown in FIG. 13, if the inputted position of lesion area belongs to the lung in the column of organ name 201, and the luminance value at the position of lesion area inputted as characteristic information 203 of the position of lesion area is −50 which falls with in the range from −2000 to 0, four character strings of bracket, pneumothorax, lung emphysema, and bronchodilation are determined from among lesion character candidates 205 as the corresponding lesion character candidates 205A. In the case where the luminance value is 100 which falls in the range from 50 to 150 and also in the range from 100 to 1000, so that nodule, GGO, infiltrative shadow, and calcification are determined as the lesion character candidates. As shown in FIG. 13, lesion character candidates 205A are displayed on image reading report generation screen 100 as lesion character candidate list 210 when the position of lesion area is specified by the user. When a lesion character candidate 210A is selected from the lesion character candidate list 210 by the user, the selected lesion character candidate 210A is inserted in the image reading report as the lesion character. In the case where a character string not included in the lesion character candidates is to be inputted, "other" shown in FIG. 14 may be selected, and the character string may be inputted from the input section. The display of the lesion character candidate list may be in the form of a pull-down menu or any other method which allows selection of a region name.

Further, an average, dispersion, or pattern of luminance values adjacent to the position of lesion area may be obtained as information to be obtained from the lesion position, and characteristic information 203 may be provided according to the average, dispersion, or pattern of luminance values adjacent to the position of lesion area, thereby allowing the corresponding lesion character candidate to be selected.

Next, lesion storage means 20 stores lesion information at lesion position 115A (ST104). The lesion information may be, for example, (1) lesion ID (2) position information of lesion area constituted by series name, slice name, and coordinates on the slice and (3) lesion character. The lesion ID and position information of lesion area constituted by series name, slice name, and coordinates on the slice may be obtained from the position information inputted from input section 303.

A medical image that includes the position 115A of lesion area obtained from input section 303 and the lesion character 105A linked by a hyperlink are inserted in finding field 105 (ST105). Here, the lesion character 105A is inserted in a manner so as to be distinguishable from the other characters, such as coloring of the lesion character, coloring of the background, or use of underline, blinking, boldface, different font type or size, or frame for the lesion character, thereby indicating that the lesion character is linked by a hyperlink.

Then, if a position of lesion area is inputted in the same manner as in step ST102 (ST106 is YES), the steps from ST103 to ST105 are repeated. That is, if a plurality of lesion positions is specified in the medical image V, the corresponding number of lesion characters is inserted.

If a further lesion position is not inputted (ST106 is NO), lesion character insertion is completed.

In the case where the lesion character inserted in image reading report generation area 105 is selected by input section 303, that is, if the lesion character 105A is selected, for example, by selection tool 123 shown in FIG. 5 or the like, medical image display means 60 obtains position information of a medical image 115 corresponding to the lesion character 105A from lesion storage means 20 and displays the medical image 115 in detailed image display area 113. Further, link information display means 40 obtains a position 115A of lesion area from lesion storage means 20 and displays the position 115A of lesion area corresponding to the lesion character 105A in the medical image in the detailed image display area. In the case where the position of the lesion area is displayed as an area, the indicator may be displayed as the representative point in the area. The display form of the indicator may be made selectable from arrow, area, pointer for pointing a representative point in the lesion area, and the like.

A process for changing a lesion character inserted in the image reading report according to the present embodiment will be described with reference to FIGS. 6 and 7.

Figure 6:
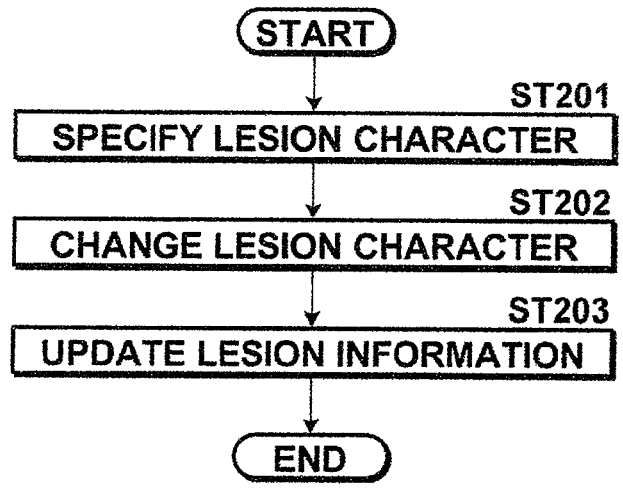
FIG. 6 is a flow diagram illustrating a process flow for changing a lesion character according to the first embodiment.

FIG. 6 is a flow diagram illustrating a process flow for changing a link character according to the first embodiment.

Figure 7:
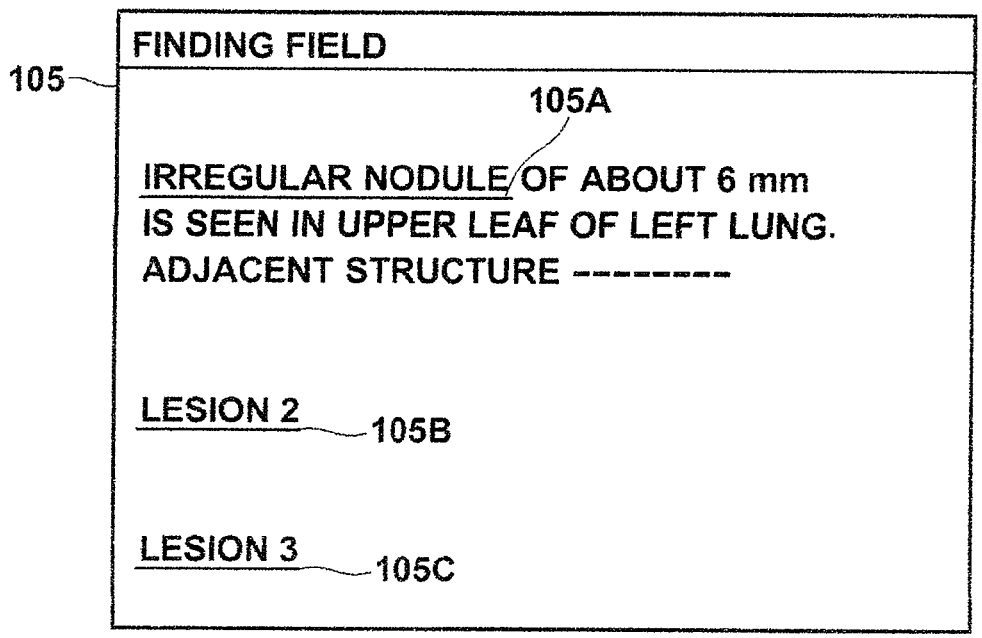
FIG. 7 is a conceptual diagram of a radiological report generated by changing a portion of the lesion character according to the first embodiment.

FIG. 7 is a conceptual diagram of a radiological report generated by changing a portion of the link character according to the first embodiment.

FIG. 7 shows, by way of example, finding field 105 of image reading report generation screen 100. FIG. 7 shows that three lesion characters of "lesion 1", "lesion 2" (105B), and "lesion 3" (105C) are inserted in the finding field, in which lesion 1 has been edited and changed to a new lesion character of "irregular nodule" (105A).

In finding field 105 in which lesion characters are inserted, one of the lesion characters is selected by input section 303 (ST201). Then, the selected lesion character is changed to a desired character string, symbol, or numeric character by operating the mouse or keyboard. More specifically, if a selection tool such as arrow 123 is pointed on the lesion character and the right mouse button is clicked, lesion character change options are displayed in a pull-down menu format. Thus, the lesion character is changed by selecting one of the lesion character change options (ST202). The lesion character may be changed using a different method, as appropriate, as long as it allows only the character string of the lesion character to be changed with the hyperlinked state being maintained. Then, the position of the lesion area corresponding to the original lesion character is linked to the new lesion character by a hyperlink and corresponding lesion information is updated (ST203).

In this way, the image reading report used in the first embodiment is generated. Further, the medical image that includes the position of lesion area associated with the lesion character is a first medical image used in the first embodiment.

Figure 9:
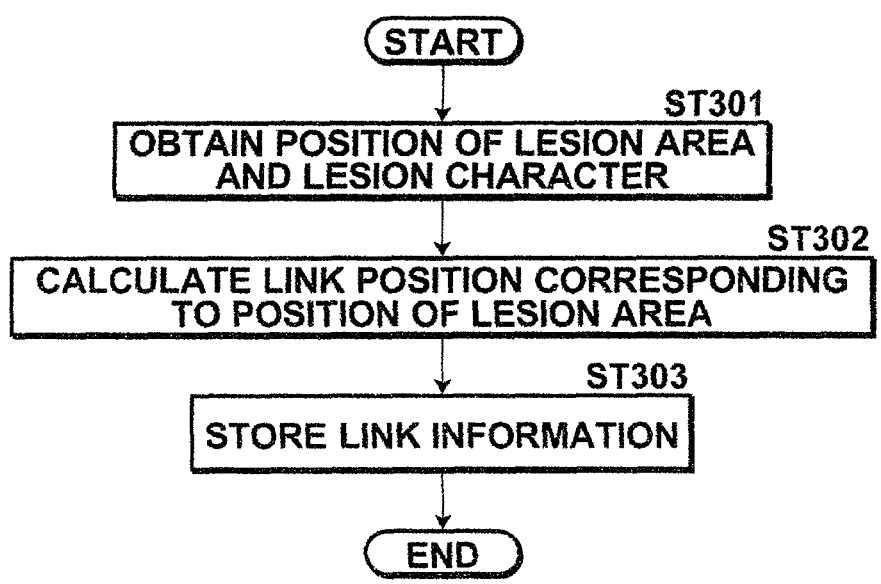
FIG. 9 is a flow diagram illustrating a process flow for inputting a link position of the first embodiment.

Next, in the medical image display method of the present embodiment, a method of displaying link information in a medical image will be described with reference to FIG. 9. FIG. 9 a flow diagram illustrating a process flow for generating link information in the medical image display method of the present embodiment.

First, link position storage means 30 obtains a lesion position in a slice image 115 and a corresponding lesion character from lesion storage means 20 (ST301). Then coordinates in a medical image 133 reconstructed by stacking a plurality of slice images, including the slice image 115 (ST302). Typical reconstructed images include those represented by volume rendering, ray summation, maximum intensity projection (MIP), and multi planar reformat (MPR).

As a three-dimensional image is reconstructed from multiple slice images, i.e., multiple two-dimensional images sliced at a predetermined thickness, coordinates of the position of a point specified in any of the two-dimensional images in the three-dimensional image may be calculated from the slice position and coordinates of the point, and the coordinate position in the three-dimensional image corresponding to the coordinates of the lesion position in the slice image is identified. Thus, the lesion position specified in the slice image can be represented in the three-dimensional image.

Then, link position storage means 30 stores the coordinate values and corresponding lesion character in association with each other as link information (ST303). The link information may be constituted by, for example, (1) link ID (2) link position which is the position in the reconstructed image 133 corresponding to the lesion position in the slice image (3) link character and (4) corresponding lesion ID. The lesion ID may be obtained from the lesion information inputted from lesion storage means 20.

Figure 8:
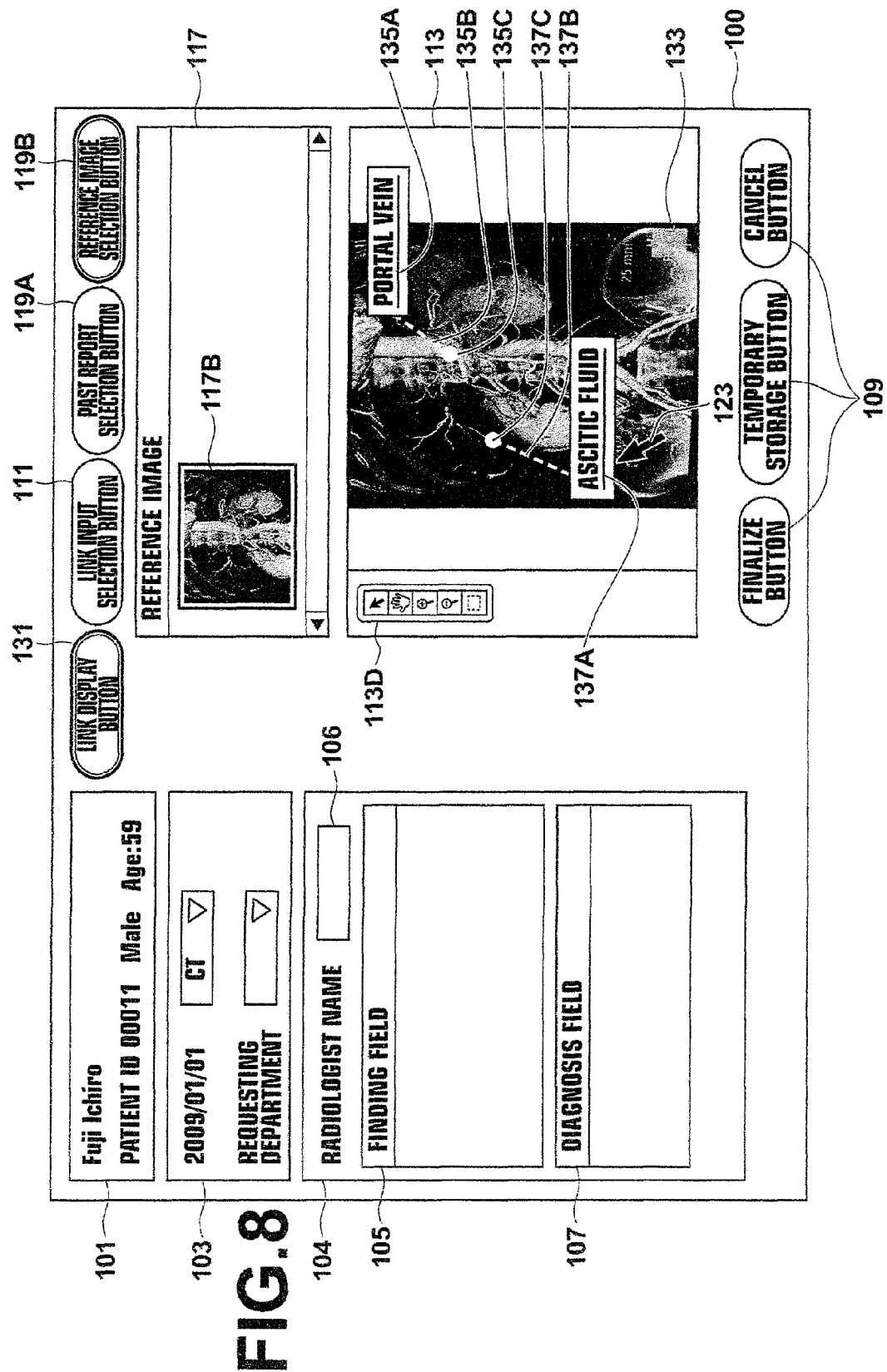
FIG. 8 is a conceptual diagram of a medical image display screen displayed according to the first embodiment.

Next, an indicator is displayed at the lesion position in the reconstructed image using FIG. 8. FIG. 8 is a conceptual diagram of a medical image display screen displayed according to the first embodiment.

The layout of medical image display screen 110 shown in FIG. 8 will be described. In medical image display screen 110 shown in FIG. 8, reference image selection button 119B is selected and a thumbnail 117B of a reference image is displayed in reference image area 117. The thumbnail 117B of a reference image in reference image area is selected and an image 133, which is a reconstructed second medical image corresponding to the selected thumbnail image 117B, is displayed in detailed image display area 113. Selection tool 113D is provided in detailed image display area 113 in which the reconstructed second medical image 133 is displayed to allow the reconstructed image 133 to be observed by changing the size and angle thereof. The medical image display screen includes link display button 131 for displaying link information. Here, the link display button 131 is selected, and link information, i.e., link characters 135A, 137A, link positions 135C, 137C, and association indicators 135B, 137C are displayed.

The link position 135C obtained from link position storage means 30 and the link character 135A constituted by lesion character 105D corresponding to the link position 135C is inserted in the reconstructed medical image 133 (ST307). In the case where positions of a plurality of lesion areas in a medical image V are stored in link position storage means 30, link characters and link positions corresponding to all of the positions of the plurality of lesion areas are displayed. In FIG. 8, positions of two lesion areas are stored in link position storage means 30 so that link characters 135A, 137A and link positions 135C, 137C are displayed. Here, the link character and the corresponding link position are displayed in association with each other. In FIG. 8, the link character 135A and the corresponding link position 135C are associated by the association indicator 135B while the link character 137A and the corresponding link position 137C are associated by the association indicator 137B.

The association between the link character and corresponding link position is not necessarily implemented by the association indicator, and they may be displayed in any manner as long as it allows identification of which link character corresponds to which position indicator. For example, the link character 135A may be displayed adjacent to the corresponding position indicator 135C. In the case where the link character and the corresponding position indicator are distinguishable, such as the case where only one link character and only one position indicator are displayed, the association indicator is not required or the link character is not required to be displayed adjacent to the position indicator.

In this way, the display of link positions 135C, 137C, and link characters 135A, 137A in the medical image allows the position of the lesion area and character string representing the lesion area described in the image reading report to be referenced simply by observing the medical image. Then, from the link positions 135C, 137C, the positions of the lesion areas may be accurately recognized, and from the link characters 135A, 137A, the lesions may be assessed easily.

In the conventional technologies, it has been difficult to accurately understand as to which position in the medical image the lesion described in the image reading report corresponds to, as one medical image is linked to one character string in the image reading report. In contrast, the present embodiment displays a link position using a position indicator so that the position of the lesion area may be accurately recognized.

Further, the link positions 135C, 137C and link characters 135A, 137A are respectively associated with each other in a medical image, so that even when a plurality of link characters and a plurality of link positions are displayed at the same time, the correspondence relationship between each link position and each link character may be recognized easily. As a result, the positions of a plurality of lesion areas and character strings representing a plurality of corresponding lesions may be recognized at a time by simply observing the medical image, whereby the diagnosis may be made more easily. Further, the relative position between link positions 135C and 137C may be recognized easily.

Further, the display of the link position in the reconstructed medical image allows the position of lesion area in a slice image to be recognized by a different medical image, so that the position of the lesion area may be recognized more accurately. In the case where a link position is displayed in a reconstructed three-dimensional image, the position of the lesion area may be recognized stereoscopically, and accurate radiological image reading may be performed base on the lesion area. Further, the reconstructed three-dimensional image may be made rotatable and scalable, and the link position and link character may be displayed in an interlocking manner with the rotation and scaling. In this case, the position of the lesion area may be viewed from a different angle with a different size, thereby allowing more accurate radiological image reading.

Figure 11:
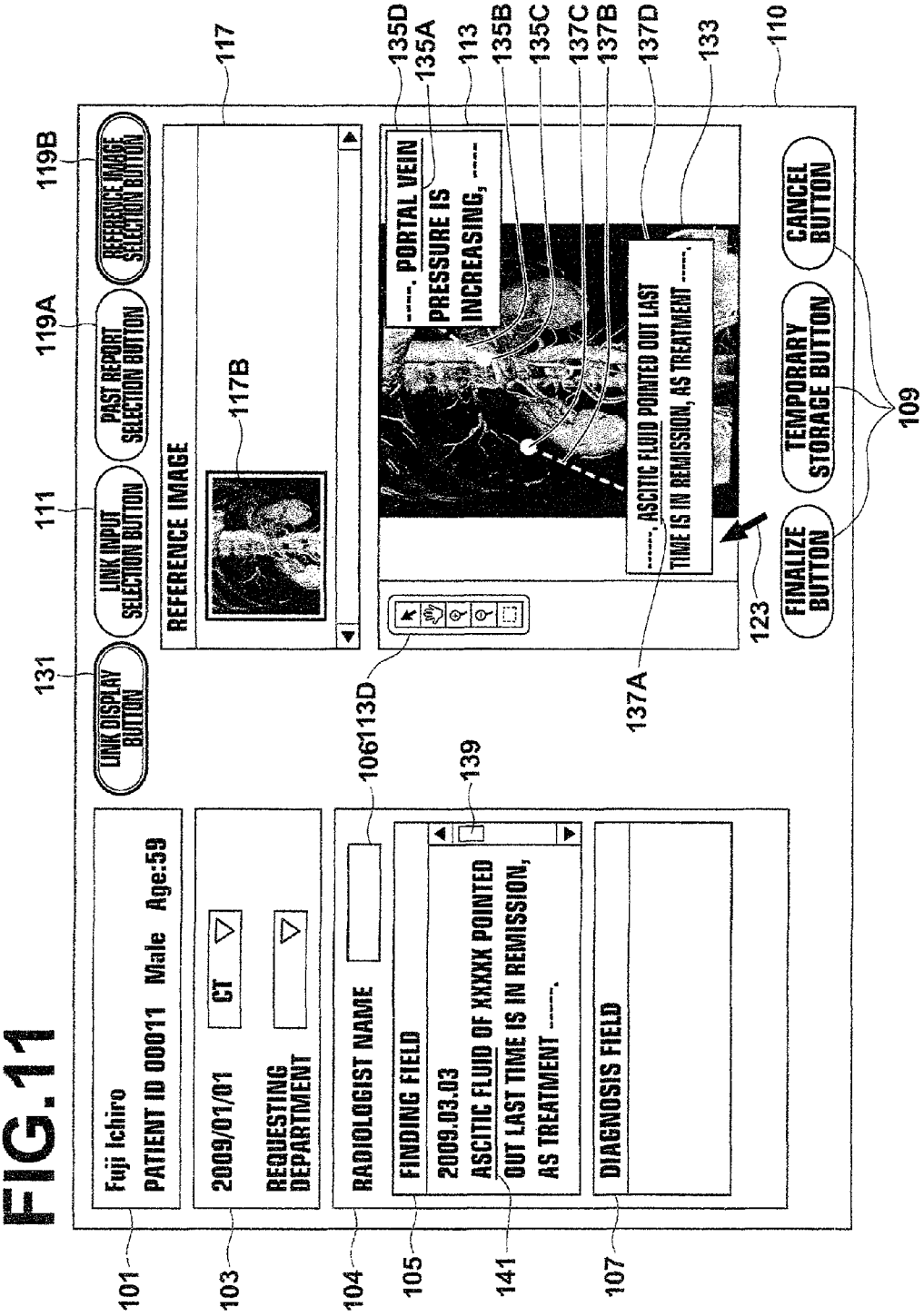
FIG. 11 is a conceptual diagram of a medical image display screen displayed according to the second embodiment.

In FIG. 8, only the link character 135A is displayed, but lesion storage means 20 may be a means that further stores a word or phrase before and after the lesion character in the image reading report as the lesion information, link position storage means 30 may be a means that further obtains the word or phrase before and after the lesion character in the image reading report from lesion storage means 20, and link information display means 40 may be a means that displays the word or phrase before and after the link character in addition to the link character 135A as shown, by way of example, in 135D in FIG. 11. For example, ten characters before the link character and ten characters after the link character may be extracted and displayed or one sentence, including the link character, may be extracted and displayed.

In this way, where a word or phrase before and after the link character is displayed in a medical image together with the link character, more detailed information may be obtained directly from the medical image and the diagnosis may be made easily. It is highly likely that before or after a link character representing a lesion in an image reading report includes a description of the lesion, so that it is highly likely that information useful in understanding the lesion is displayed by displaying the word or phrase before and after the link character, whereby the diagnosis may be assisted greatly.

Further, in the case where a plurality of link characters and a plurality of lesion areas are present, it is necessary that the correspondence relationship between each link character and each lesion area corresponding to each other is made clear. Therefore, it is desirable to use an indicator for indicating the correspondence relationship, such as drawing a leading line between a corresponding pair or coloring the correspond pair with the same color which is different from that used for a different corresponding pair. Such a distinguishable display as in the manner described above allows the correspondence between the link character and link position to be made clear, resulting in easy understanding of the image reading report.

Figure 10:
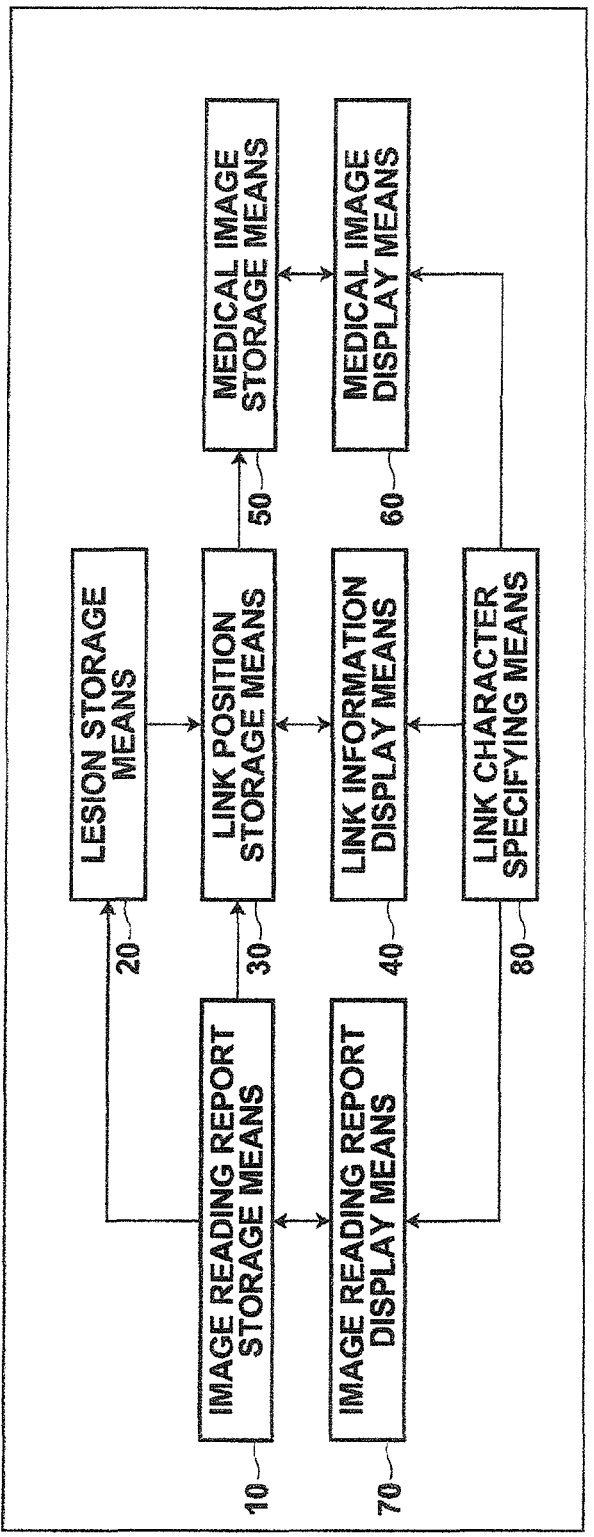
FIG. 10 is a functional block diagram of a medical image display function of a second embodiment.

A configuration of a second embodiment will now be described with reference to FIG. 10. FIG. 10 is a functional block diagram of a medical image display function of the second embodiment. The configuration shown in FIG. 10 is identical to that shown in FIG. 3 except that the configuration in FIG. 10 further includes image reading report display means 70 and link character specifying means 80. Therefore, identical portions will not be elaborated upon further here.

Image reading report display means 70 is mainly constituted by display section 301 for displaying an image reading report and displays an image reading report stored in image reading report storage means 10 on display section 301 in response to the specification by link character specifying means 80.

Link character specifying means 80 is mainly constituted by input section 303 for inputting a lesion area and in response to the specification of a link character or a lesion character by the operator via input section 303, inputs the specified link character to either one of link information display means 40, medical image display means 60, and image reading report display means 70.

Further, in the second embodiment, link information display means 40 displays the link character 137A in the medical image by linking the character to the corresponding lesion character 141 described in the image reading report by a hyperlink.

By way of example, a medical image display according to the second embodiment will be described with reference to FIG. 11. FIG. 11 shows, by way of example, medical image display screen 110 according to the second embodiment. In medical image display screen 110 shown in FIG. 11, a phrase before and after the lesion character 141 described in the image reading report is displayed in addition to the link character 137A, as shown in a comment 137D. Likewise, in addition to the link character 135A, a phrase before and after the lesion character corresponding to the link character 135A described in the image reading report is displayed, as shown in a comment 135D. Components given the same reference numerals as those in FIG. 8 are identical and will not be elaborated upon further here.

In FIG. 11, as the specified link character 137A is linked by a hyperlink to the image reading report that includes the lesion character 141, image reading report display means 70 displays the image reading report, that includes the lesion character 141, in finding field 105 in response to the specification of the link character 137A with selection tool 123 of link character specifying means 80. In finding field 105, by way of example, only a portion of the report adjacent to the lesion character 141 is displayed and it is indicated that the entire image reading report may be referenced by moving cursor 139. Note that, however, the display method of the image reading report is not limited to this, and the image reading report may be displayed in a separate window or in its entirety in response to the specification of the link character 137A.

As described above, the link character 137A and image reading report that includes lesion character 141 are linked by a hyperlink, so that by simply specifying the link character 137A in the image, the corresponding detailed information in the image reading report may be referenced easily, thereby allowing an efficient diagnosis.

Figure 12:
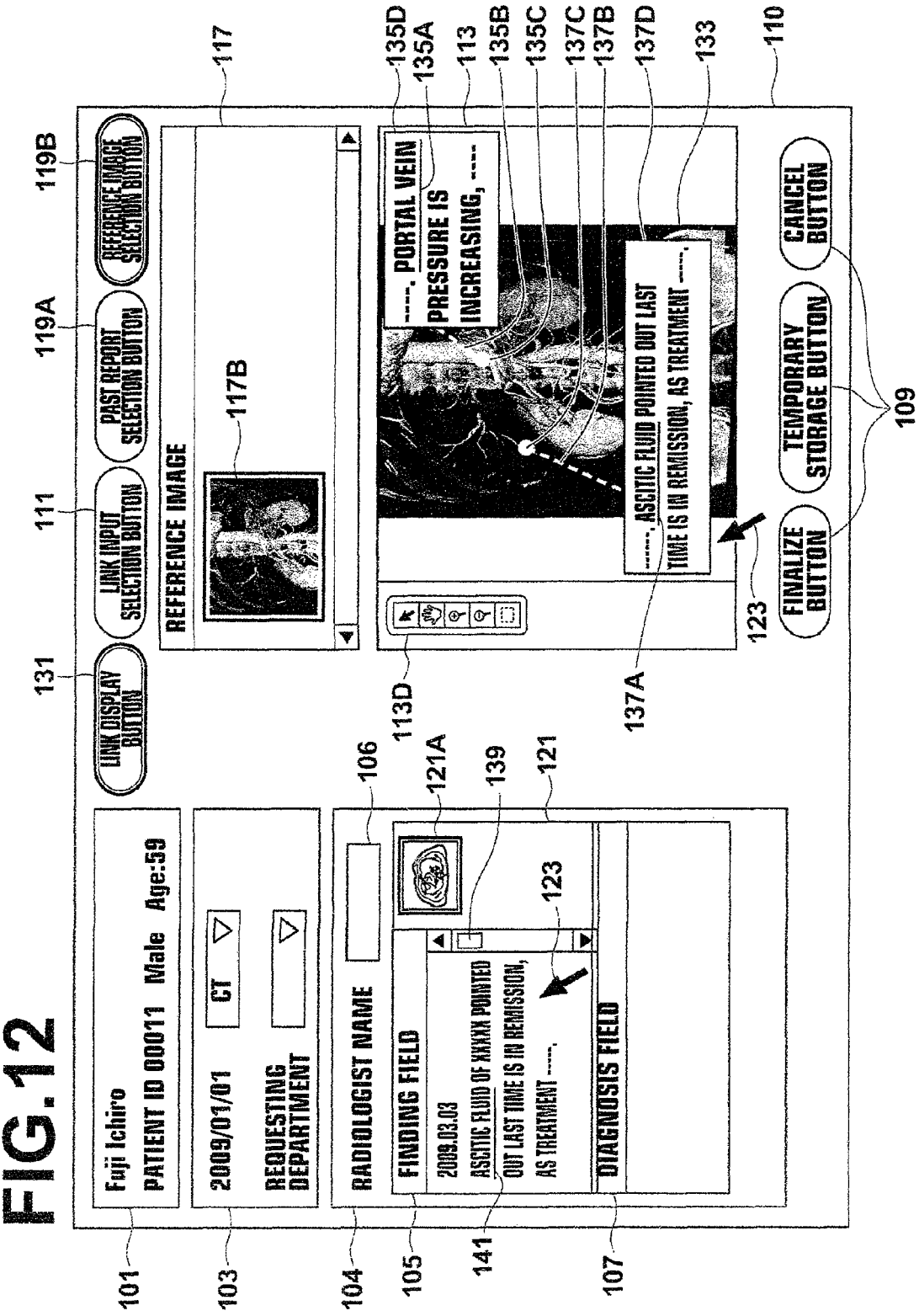
FIG. 12 is a conceptual diagram of a medical image display screen displayed according to a third embodiment.

By way of example, a medical image display according to a modification of the second embodiment will be described with reference to FIG. 12. FIG. 12 shows, by way of example, medical image display screen 110 according to the modification of the second embodiment. Components given the same reference numerals as those in FIG. 11 are identical and will not be elaborated upon further here. In the modification of the second embodiment, the lesion character 141 described in the image reading report and a slice image 121A, which is the first medical image corresponding to the lesion character 141, are linked by a hyperlink.

In FIG. 12, as specified lesion character 141 is linked by a hyperlink to the slice image 121A, which is the first medical image, including the position of the corresponding lesion area, medical image display means 60 displays a thumbnail of the slice image 121A in attached image display area 121 in response to the specification of the lesion character 141 with selection tool 123 of link character specifying means 80. Further, in response to the specification of the lesion character 141, indicator 147 (not shown) is displayed in the slice image 121A by link information display means 40. Note that, however, the display method of the medical image that includes the position of lesion area is not limited to this, and the slice image 121A may be displayed in a separate window or as a detailed medical image instead of the thumbnail in response to the specification of the lesion character 141.

As described above, the lesion character 141 and slice image 121A are linked by a hyperlink, so that by simply specifying the lesion character 141 in the image reading report, the corresponding slice image 121A may be referenced easily, thereby allowing an efficient diagnosis. According to the second embodiment, from the link character 137A in the reconstructed medical image 133, the corresponding lesion character 141 in the image reading report may be referenced, and from the lesion character 141, the corresponding slice image 121A may be referenced, the corresponding detailed information may be obtained easily, thereby allowing an efficient radiological image reading.

Preferably, in response to the specification of the link character 137A, the specified link character 137A and the position 137C of lesion area are displayed in a distinguishable manner from the other link character 135A and link position 135C. This allows clear understanding as to which link character 137A is specified, whereby it is easy to understand that the image reading report corresponding to the link character 137A is displayed.

Further, the link character and the position of the corresponding lesion area may be highlighted by various methods for displaying in a distinguishable manner, such as blinking of the mark, character, or both, coloring of the link character or background, or use of underline, blinking, boldface, different font type or size, or frame for the link character. As a result, it is clear that the displayed position of lesion area corresponds to which link character, whereby the image reading report may be understood more easily.

Next, a third embodiment will be described. Image reading report storage means 10 stores a plurality of image reading reports, including past image reading reports with respect to past medical images of the same patient. Lesion storage means 20 converts a lesion position in a past medical image to the corresponding lesion position in a current image representing the same region and same position and stores as lesion information. More specifically, with respect to a slice image 143 representing a lesion position in a past medical image, a medical image constituted by a group of tomographic images, including the past slice image 143, is aligned with a medical image constituted by a group of current tomographic images using the technique described in Japanese Unexamined Patent Publication No. 2009-72432 of the present inventor and coordinates representing the lesion position in the slice image 143 are obtained as the coordinates of attention point in the corresponding current medical image 145. Then, the coordinates of the lesion position in the current medical image 145, which is the first medical image, are stored as lesion information.

Further, lesion storage means 20 further associates image reading report identification information for identifying the image reading report that includes the lesion character with the lesion information and stores the resultant information. The image reading report identification information is constituted by information capable of identifying the image reading report, such as the file name of the report, data of the report, and the like.

In this case, link position storage means 30 obtains the lesion information from lesion storage means 20, associates the image reading report identification information with the link information, and stores the resultant information. Link information display means 40 displays the past lesion character and current lesion character in a distinguishable manner based on the image reading report identification information. For example, the date of image reading report may be displayed in the reconstructed medical image as the image reading report identification information, in addition to the link character. Further, when displaying the corresponding image reading report in response to the specification of the link character 137A, the image reading report identification information, such as the date of image reading report or the like may be displayed in addition to the image reading report by applying the second embodiment to the third embodiment.

This allows link information display means 40 to display a past lesion character representing a lesion described in a past image reading report in a reconstructed second medical image, whereby a lesion position corresponding to the past lesion position may be referenced easily in the current medical image. As a result, a diagnosis with reference to the progress of the past lesion may be made easily and image reading may be performed efficiently.

In the case where image reading report identification information is displayed in a reconstructed medical image, it is easy to identify in which image reading report the information is described, whereby the diagnosis of the progress of the lesion may be made easily. For example, in the case where the date of the report is displayed in the medical image, a diagnosis may be made in consideration of the passage of time from the date of the report, resulting in an accurate image reading.

In the case where a past image reading report is displayed together with the image reading report identification information by applying the second embodiment to the third embodiment, it is easy to identify in which image reading report the information is described, whereby the diagnosis of the progress of the lesion may be made easily. For example, in the case where the date of the report is displayed in the medical image, a diagnosis may be made in consideration of the passage of time from the date of the report, resulting in an accurate image reading.

The second medical image reconstructed from a plurality of medical images, including the first medical image, may be more than one. Hereinafter, a fourth embodiment in which a plurality of second medical image is provided will be described.

In the case where a plurality of second medical images is provided, each second medical image is a medical image reconstructed by a different reconstruction method or a medical image different in display position and size from each other. Images reconstructed by various methods, such as volume rendering, surface rendering, ray summation, maximum intensity projection (MIP), multi planar reformat (MPR), minimum intensity projection (MNIP), curved planar reformation (CPR), and the like, may be applied to the second medical image.

Figure 15:
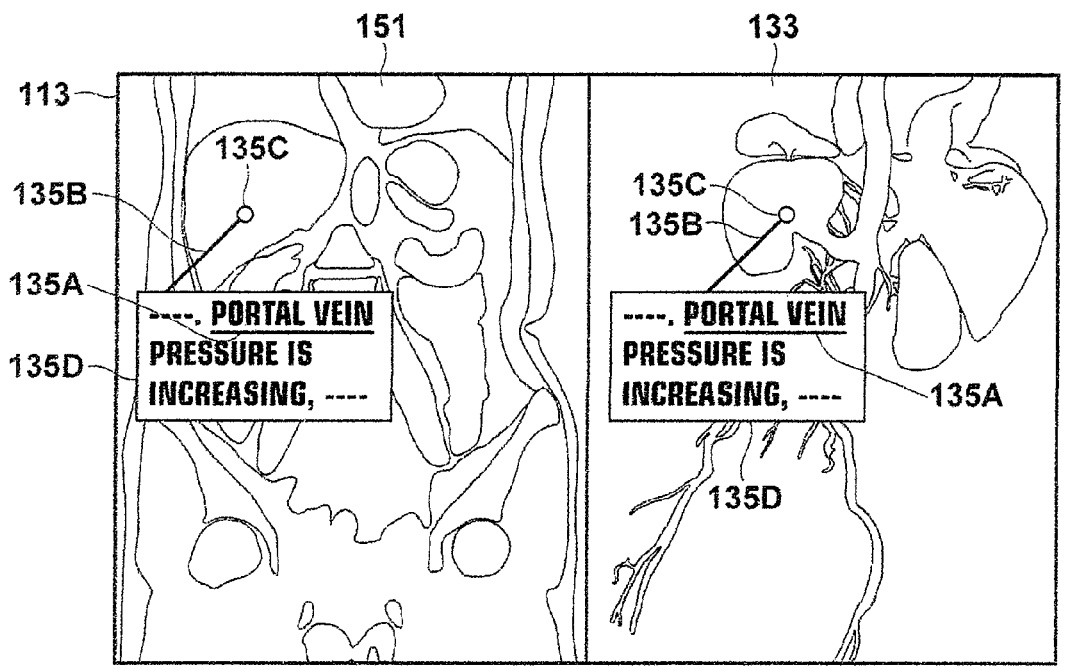
FIG. 15 illustrates a medical image display screen displayed according to a modification of the first embodiment.

A specific description will be made with reference to FIG. 15. FIG. 15 illustrates a medical image display screen displayed according to a modification of the first embodiment. FIG. 15 shows only detailed image display area 113 shown in FIG. 8. As shown in FIG. 8, the thumbnail 117B of a reference image in reference image area 117 is selected, and an image represented by volume rendering (VR), which is a reconstructed second medical image 133 corresponding to the selected thumbnail 117B, and an image represented by MPR, which is a second medical image 151 corresponding to the selected thumbnail image, are displayed in the detailed image display area 113 as shown in FIG. 15. Note that the second medical images 133 and 151 are generated from the same image data. Then, link information of link character 135A, link position 135C, and association indicator 135B is displayed in both images, one of which is represented by VR and the other of which is represented by MPR. In FIG. 15, in addition to the link character 135A, a phrase before and after the lesion character 141 described in the image reading report is further displayed in comment 135D.

In FIG. 15, the same link information is displayed in each of a plurality of second medical images, but the display method is not limited to this, and the link information may be selectively displayed according to the type of each of the second medical images, such as VR, MIP, or the like. For example, a selective display option may be provided with respect to each link character and if VR is set to the selective display option, the link information may be displayed only in an image represented by VR method, while if MIP is set to the selective display option, the link information may be displayed only in an image represented by MIP method. In the case where the link information is associated with lesion characters of a plurality of image reading reports, the selective display option may be set with respect to each image reading report. More specifically, image reading report identification information for identifying each image reading report, such as the date and time of each image reading report or the like, may be set as the link information, and the same selective display option is set to the same link information.

As described above, according to the fourth embodiment, by displaying link information in each of a plurality of second medical images constructed from a plurality of medical images, including the first medical image, an image diagnosis may be made using a plurality of reconstructed medical images with respect to the same lesion, whereby the image reading may be made more efficiently and accurately. In the case where the link information is selectively displayed with respect to the type of second medical image, only necessary information may be displayed on the second medical image according to the type of second medical image, resulting in a more efficient and accurate image reading.

As a modification of the fourth embodiment, a configuration may be adopted in which, in one of the second medical images, display of another second medical image is selectable from GUI, and the another second image is displayed instead of or in addition to the one of the second medical image on medical image display means 60 in response to the selection to display the another second image. For example, a configuration may be adopted in which when the right button of the mouse is clicked on a second medical image represented by VR method, display methods, including MIP, MPR, and the like, are selectably displayed in a pull-down menu, and if MIP is selected by the user from the pull-down menu using the mouse or the like, another second medical image represented by MIP method is displayed instead of the second medical image represented by VR method.

Further, as another modification of the first embodiment described in the present specification, in the case where the second medical image has time series image data, the second medical image may be displayed four-dimensionally with the link information being displayed at the link position of the second medical image.

Figure 16:
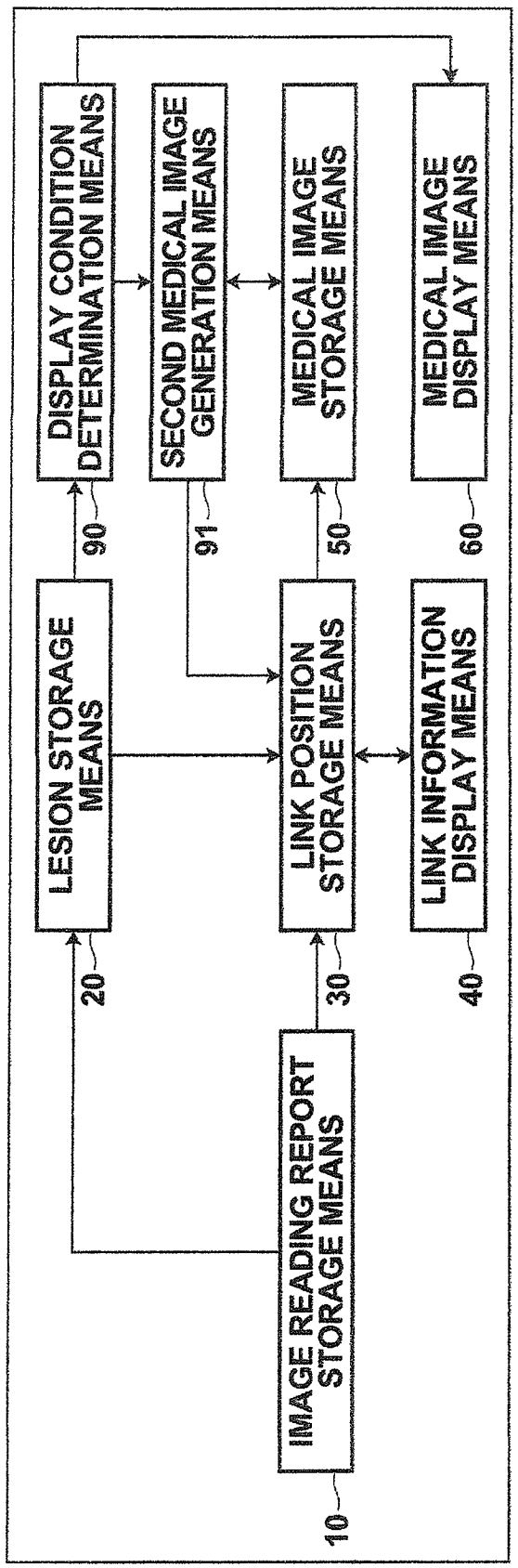
FIG. 16 is a functional block diagram of a medical image display function of a fifth embodiment.

Next, a fifth embodiment will be described with reference to FIG. 16. FIG. 16 is a functional block diagram of the fifth embodiment. As illustrated in FIG. 16, the fifth embodiment further includes display condition determination means 90 for obtaining a lesion character described in an image reading report from lesion storage means 20, extracting a keyword corresponding to the lesion character, and determining the display condition from the extracted keyword, and second medical image generation means 91 for generating a second medical image based on the determined display condition and storing the generated second medical image in medical image storage means 50. Further, medical image display means 60 according to the fifth embodiment displays the second medical image based on the determined display condition.

FIG. 17 illustrates display condition determination means 90 broken into functional blocks. As illustrated in FIG. 17, display condition determination means 90 includes keyword table 93, keyword extraction section 92, display condition table 94, and display condition determination section 95.

Keyword extraction section 92 obtains a lesion character described in an image reading report from lesion storage means 20 and extracts keywords K1, K2 serving as a display condition determinant factor using keyword table 93. FIG. 18 shows, by way of example, keyword table 93. As shown in FIG. 18, keyword table 93 is a table in which keywords and lesion characters are associated and information of anatomical structures and lesions are registered as lesion characters and extraction target words. Keyword extraction section 92 obtains a lesion character registered in the lesion information from lesion storage means 20. In this example, it is assumed that "left lung" and "nodule" are obtained as the lesion characters in the lesion information. Next, keyword extraction section 92 converts a lesion character hit by searching to a keyword. That is, "left lung" is converted to "lung" (keyword K1) which is associated with various words, while the "nodule" becomes a keyword "nodule" (keyword K2) as-is.

The keyword extraction method is not limited to that described above, and it is possible to employ any known natural language processing techniques such as those used in search engines. But, the searching using the keyword table described above is sufficiently effective if the names of anatomical structures and lesions are standardized by providing a user interface for selectively inputting anatomical structures and lesions when generating an image reading report. In the fifth embodiment, keyword extraction section 92 may directly use a lesion character as a keyword without providing the keyword table. Provision of the keyword table, however, allows one keyword to be associated with a plurality of lesion characters, so that the display condition for various lesion characters may be set efficiently without unnecessarily increasing the number of keywords registered in the display condition table.

Then, using the keywords K1, K2 extracted by keyword extraction section 92, display condition determination section 95 identifies the display condition associated with these keywords K1, k2 by reference to display condition table 94 for determining image processing method for generating and displaying a second medical image from a plurality of medical images, including a first medical image, and/or determining the display mode of the second medical image.

Such display conditions can be maintained by the users of doctors of the diagnosis and treatment department, or the like by performing registration, modification, and deletion. The maintenance may be directly performed on display condition table 94, but it is preferable that the maintenance may be implemented through a GUI for interactively performing input or selection operations for the contents of the display condition table. Further, it is also desirable that the display condition for the currently displayed image may be confirmed from the GUI. The reason is that this will facilitate understanding of the users at the time of image diagnosis and operability for editing display condition table may be improved.

Preferably, display condition table 94 includes display conditions associated with each keyword, such as VR color template, parameters of gradation and emphasis processing, window width of medical image, window level, image recognition processing using CAD and the like. Here, VR color template is a template for determining the VR color display mode in which RGB or opacity is set in association with the density value of the image data.

FIG. 19 shows, by way of example, display condition table 94a. For example, if the lesion character is a character indicating blood vessel abnormality, display condition determination means 90 extracts "blood vessel" as the keyword from the keyword table, and determines the display condition "101" corresponding to the keyword "blood vessel" from display condition table 94a. Then, display condition determination means 90 outputs the determined display condition "101" and lesion character "blood vessel" to second medical image generation means 91.

Second medical image generation means 91 obtains the display condition "101" and lesion character "blood vessel" from display condition determination means 90 and obtains image data that include a first medical image associated with the lesion character "blood vessel" by reference to lesion storage means 20. Then, based on the image type "VR" associated with the display condition "101", second medical image generation means 91 generates a second medical image by the VR method from the obtained image data and stores the generated second medical image in medical image storage means 50. The second medical image is stored in medical image storage means 50 with information identifying the display condition of the second medical image, for example, display condition ID "101", being associated by tag information or the like. In the case where the type of second medical image is determined in association with the keyword in the manner as described above, the second medical image may be generated by the reconstruction method appropriate for the lesion or organ and displayed, resulting in more efficient and accurate image reading.

Then, when an instruction to display the second medical image is received by way of user input or the like, medical image display means 60 obtains the second medical image and information identifying the display condition of the second medical image, such as display condition ID "101", from medical image storage means 50, obtains display condition "101" from display condition determination means 90, and displays the second medical image based on the display condition "101". Determined display condition "101" associated with the keyword "blood vessel" sets "VR" as the type of second medical image, coordinates of starting point and widow size "(0, 0), W=512, H=512" as the display position information of display window of the second medical image, and VR color template "Cr1" as the color template. Therefore, medical image display means 60 obtains the second medical image reconstructed by the VR method from medical image storage means 50 and displays the image in a window of W=512 and H=512 from coordinates (0, 0) by applying the VR color template Cr1.

Further, for example, with respect to each organ, a color template that best displays each organ may be provided. For example, if the link character is "liver", color template Cr2 provided for livers is selected and the liver is displayed by the VR method based on the selected color template Cr2. As the second medical image is displayed according to the lesion character, more efficient and accurate image reading may be performed.

Further, medical image display means 60 may be a means that displays the second medical image centered on the link position in the image. For example, medical image display means 60 may be a means that obtains the link position from link position storage means 30 and, based on the display condition obtained from display condition determination means 90, displays the second medical image in a display window of a specific size disposed at a specific position such that the link position comes to the center of the display window.

By displaying the second medical image such that the link position comes to the center of the display window, the second medical image may be displayed such that the position of lesion area is visually recognized easily, so that more efficient and accurate image reading may be performed. Note that the second medical image is not necessarily displayed such that the position of lesion area comes to the center of the display window as long as the position of lesion area is visually recognized easily.

As a modification of the fifth embodiment, in the case where the second medical image has already been generated and stored in medical image storage means 50, and the display condition table is not a table in which an image type is associated with a keyword, second medical image generation means 91 is not required since it is not necessary to generate the second medical image. More specifically, display condition determination means 90 obtains a lesion character described in an image reading report from lesion storage means 20, then extracts the keyword corresponding to the lesion character, and determines the display condition for the second medical image from the extracted keyword. Then, medical image display means 60 may display the second medical image already generated and stored in medical image storage means 50 based on the determined display condition.

A further modification of the fifth embodiment will be described with reference to FIG. 20. FIG. 20 shows, by way of example, a display condition table 94b of the further modification of the fifth embodiment. As shown in FIG. 20, in the further modification of the fifth embodiment, the medical image display apparatus further includes a plurality of CADs of different types and the display condition table 94b is a table in which image processing using automatic recognition processing by CAD is set in association with each keyword. For the extraction of an organ or lesion using CAD, various known automatic recognition techniques, including the examples described above, may be used.

In the further modification of the fifth embodiment, if the lesion character is, for example, a character representing a cardiac lesion, display condition determination means 90 extracts a keyword "heart", and determines a display condition "201" corresponding to the keyword "heart" from the display condition table 94b. The display condition "201" includes cardiac extraction and coronary artery extraction, and distinguishable display of the extracted heart and coronary artery in association with the keyword "heart". Medical image display means 60 performs cardiac extraction and coronary artery extraction on a second medical image obtained from medical image storage means 50 based on the display condition "201" and displays the second medical image with the extracted heart being displayed in a distinguishable manner and the extracted coronary artery of the heart being displayed in a further distinguishable manner.

Here, an option for hiding an anatomical structure, such as the extracted organ or the like, by masking the structure may be set in association with the keyword.

For example, as shown in "202" and "203" of display condition table 94b, liver extraction and "non-display other than the extracted anatomical structure" may be set in association with the keyword "liver", or spleen extraction and "non-display other than the extracted anatomical structure" may be set in association with the keyword "spleen". In this case, for example, with respect to a lesion character representing "lesion of liver and spleen", display condition determination means 90 extracts keywords "liver" and "spleen" from keyword table 93, and determines display conditions "202" and "203" from the display condition table 94b. Medical image display means 60 obtains the determined display conditions "202" and "203" from display condition determination means 90, obtains a plurality of medical images, including a first medical image or a second medical image from medical image storage means 50, and extracts the liver and spleen from the obtained medical image by CAD. Then, medical image display means 60 hides an organ other than the extracted liver and spleen by masking.

Further, as shown in the display condition "204" in display condition table 94b, an option for extracting a bone by CAD and hiding the extracted anatomical structure may be set in association with the keyword "blood vessel". In this case, medical image display means 60 obtains the display condition "204", extracts a bone by CAD from the second medical image obtained from medical image storage means 50, and hides the extracted bone by masking when displaying the second medical image.

As described above, in the case where image recognition processing by CAD is set in the display condition in association with the keyword, the second image may be displayed with the lesion or organ being displayed in an easily distinguishable manner according to the keyword extracted in association with the lesion character of a lesion, organ, or the like, whereby more efficient and accurate image reading may be performed.

Embodiments described above may be applicable to other embodiments without the nature thereof being changed.

The invention claimed is:

1. A medical image display apparatus, comprising:
a medical image storage unit for storing a first medical image and a second medical image reconstructed from a plurality of medical images, including the first medical image;
an image reading report storage unit for storing an image reading report that includes a lesion character representing lesion contents of a lesion area in the first medical image;
a lesion storage unit for storing the lesion character and a position of the lesion area in association with each other;
a link position storage unit for calculating a position in the second medical image corresponding to the position of the lesion area and storing the calculated position as a link position;
a medical image display unit for obtaining the second medical image from the medical image storage unit and displaying the obtained image; and
a link information display unit for displaying a link character constituted by the lesion character and a position indicator indicating the link position corresponding to the position of the lesion area represented by the link character in the second medical image in association with each other.

2. The medical image display apparatus of claim 1, wherein the second medical image is a three-dimensional medical image.

3. The medical image display apparatus of claim 1, wherein:
the link position storage unit is a unit that stores the lesion character and a word or phrase before and after the lesion character from the image reading report stored in the image reading report storage unit; and
the link information display unit is a unit that displays the word or phrase before and after the lesion character in addition to the link character.

4. The medical image display apparatus of claim 1, wherein:
the apparatus further comprises a link character specifying unit for specifying the link character in the second medical image and an image reading report display unit for displaying the image reading report;

the link character is a character linked to the lesion character in the image reading report by a hyperlink; and the image reading report display unit is a unit that, in response to the specification of the link character in the second medical image, additionally displays the entirety of the image reading report that includes the lesion character corresponding to the specified link character with the lesion character corresponding to the specified link character in the additionally displayed image reading report being highlighted.

5. The medical image display apparatus of claim 4, wherein:

the lesion character is a character linked to the first medical image by a hyperlink;

the medical image display unit is a unit that displays the first medical image, other than the second medical image, in response to the specification of the lesion character in the additionally displayed image reading report; and the link information display unit is a unit that further displays an indicator indicating the position of the lesion area in the first medical image.

6. The medical image display apparatus of claim 4, wherein the image reading report display unit is a unit that displays, in conjunction with the image reading report, an attached image which is a reduced image of the medical image that includes the lesion area corresponding to the specified link character.

7. The medical image display apparatus of claim 1, wherein the image reading report comprises a plurality of image reading reports with respect to past medical images or with respect to a plurality of different lesion positions.

8. A medical image display method, comprising the steps of:

storing a first medical image and a second medical image reconstructed from a plurality of medical images, including the first medical image;

storing an image reading report that includes a lesion character representing lesion contents of a lesion area in the first medical image;

storing the lesion character and a position of the lesion area in association with each other;

calculating a position in the second medical image corresponding to the position of the lesion area and storing the calculated position as a link position;

obtaining the second medical image from the medical image storage unit and displaying the obtained image; and displaying a link character constituted by the lesion character and a position indicator indicating the link position corresponding to the position of the lesion area represented by the link character in the second medical image in association with each other.

9. A non-transitory recording medium on which is recorded a medical image display program for causing a computer to function as:

a medical image storage unit for storing a first medical image and a second medical image reconstructed from a plurality of medical images, including the first medical image;

an image reading report storage unit for storing an image reading report that includes a lesion character representing lesion contents of a lesion area in the first medical image;

a lesion storage unit for storing the lesion character and a position of the lesion area in association with each other;

a link position storage unit for calculating a position in the second medical image corresponding to the position of the lesion area and storing the calculated position as a link position;

a medical image display unit for obtaining the second medical image from the medical image storage unit and displaying the obtained image; and a link information display unit for displaying a link character constituted by the lesion character and a position indicator indicating the link position corresponding to the position of the lesion area represented by the link character in the second medical image in association with each other.

* * * * *